(12) United States Patent
Wei et al.

(10) Patent No.: US 8,817,996 B2
(45) Date of Patent: Aug. 26, 2014

(54) AUDIO SIGNAL PROCESSING SYSTEM AND ITS HEARING CURVE ADJUSTING UNIT FOR ASSISTING LISTENING DEVICES

(75) Inventors: Ming-Fan Wei, Taichung (TW);
Fu-Kun Chen, Taichung (TW);
Hung-Yue Chang, Taichung (TW)

(73) Assignee: Merry Electronics Co., Ltd., Taichung (TW)

( * ) Notice: Subject to any disclaimer, the term of this patent is extended or adjusted under 35 U.S.C. 154(b) by 402 days.

(21) Appl. No.: 13/286,730

(22) Filed: Nov. 1, 2011

(65) Prior Publication Data
US 2013/0108095 A1     May 2, 2013

(51) Int. Cl.
*H04R 29/00* (2006.01)
*H04R 25/00* (2006.01)

(52) U.S. Cl.
CPC ........................ *H04R 25/00* (2013.01)
USPC ............................ 381/60; 381/312

(58) Field of Classification Search
CPC ........ H04R 25/60; H04R 25/70; H04R 25/65; H04R 25/505; H04R 25/356; H04R 25/652; H04R 25/554; H04R 25/456; H04R 2225/021; H04R 2225/025; H04R 2225/41; H04R 2225/63
USPC .......................... 381/312, 328, 330
See application file for complete search history.

(56) References Cited

U.S. PATENT DOCUMENTS

2007/0239294 A1* 10/2007 Brueckner et al. .............. 381/22

* cited by examiner

*Primary Examiner* — Brian Ensey
(74) *Attorney, Agent, or Firm* — Muncy, Geissler, Olds & Lowe, P.C.

(57) ABSTRACT

An audio signal processing system for use in assisting listening devices is disposed in a digital signal processor. The audio signal processing system comprises an input signal conversion unit, a signal compression unit, a hearing curve adjusting unit and an output signal conversion unit. An external audio signal can be converted from an analog format into a digital format by the input signal conversion unit, it is then compressed by the signal compression unit to be output to the hearing curve adjusting unit for adjusting parameters of the audio signal based on a hearing curve preset value, then it is output to the output signal conversion unit for the hearing signal to be amplified and converted from the digital format into the analog format for output, the audio signal is finally converted into music or voice by speakers of an assisting listening device to be output into a user's ears.

6 Claims, 4 Drawing Sheets

AUDIO SIGNAL PROCESSING SYSTEM AND ITS HEARING CURVE ADJUSTING UNIT FOR ASSISTING LISTENING DEVICES

BACKGROUND OF THE INVENTION

1. Field of Invention

The present invention discloses an audio signal processing system and its hearing curve adjusting unit for use in assisting listening devices, which can set parameters of an assisting listening device, based on a hearing curve suitable for a user and his hearing condition.

2. Related Art

As mobile phones are becoming more popular and convenient, users are always using them to communicate with relatives, friends and business partners to keep in connection, people are so used to communicating by mobile phones that they are becoming a part of their lives. However, having mobile phones placing on ears so frequently can cause damage to hearing ability. Furthermore, because of digitalization of music, people can enjoy music anywhere and anytime by using, mobile phones, walkmans with earphones. Even though entertainment and convenience are provided, hearing ability can be damaged by loud volume and the problem is often neglected; this results in early degeneration and aging of hearing ability without realizing it, and daily life is therefore affected gradually.

Currently, patients with damaged hearing ability are usually suggested to use hearing aids to assist them in hearing. The patients have to be inspected by professionals for detailed reports on hearing ability before a suitable hearing aid can be chosen based on the inspection results and the patent's requirements. A model with suitable exterior and circuit design is decided, functions of the hearing aid can be made use of to its limitation after a period of testing and evaluation by the user.

The abovementioned hearing ability inspections include external auditory canal and eardrums, pure tone audiometry, uncomfortable loudness level, speech audiometry, tympanometry, etc. Briefly, a patient with damaged hearing ability has to go through various complicated inspections in order to have a hearing aid suitable for his hearing condition. Therefore, an expensive price is expected for such complicated tests; unless the patient's hearing ability is damaged to a certain degree; otherwise, the demand for choosing a suitable hearing aid is low, especially for those with slightly damaged hearing ability.

Therefore, a type of assisting listening device which can have hearing signals adjusted and amplified is developed and can be found in the market. The device is usually designed as an earphone and has functions similar to a hearing aid. Thus, patients do not have to go through such complicated inspections because of the functions have been simplified. However, providing of hearing signal adjusting and setting functions suitable for patients in order to allow them to have a sense of hearing which is realistically simulated, are the subjects for developers to research and study on.

SUMMARY OF THE INVENTION

In view of the abovementioned subjects, an object of the present invention discloses an audio signal processing system and its hearing curve adjusting unit for assisting listening devices, which can provide better sense of hearing for users by setting parameters based on a hearing curve in order to suit users' hearing condition.

In order to achieve the abovementioned objects, an audio signal processing system of the present invention can be disposed in a digital signal processor of an assisting listening device for processing audio signals. The audio signal processing system comprises an input signal conversion unit, a signal compression unit, a hearing curve adjusting unit and an output signal conversion unit. An audio signal can be converted from an analog format into a digital format by the input signal conversion unit; it is then compressed by the signal compression unit to be output to the hearing curve adjusting unit for adjusting parameters of the audio signal, based on a hearing curve preset value in the hearing curve adjusting unit; then it is output to the output signal conversion unit for the audio signal to be amplified and converted from the digital format into the analog format for output; the audio signal is finally converted to music or voice by speakers of an assisting listening aid to be output into a user's ears.

Furthermore, in order to set the hearing curve value, the hearing curve adjusting unit of an audio signal processing system of the present invention comprises an hearing curve integration and display module, a finite impulse response algorithmic module and an algorithmic coefficient storing and processing module. The hearing curve integration and display module is for receiving a tested hearing curve signal and a referenced hearing curve graph, and for converting the tested hearing curve signal to be shown on the referenced hearing curve graph, and displayed by a graphic interface. The tested hearing curve signal can be calculated by the finite impulse response algorithmic module to produce a filter coefficient matrix; and by adjusting the coefficients of the filter coefficient matrix, the tested hearing curve can be adjusted in order to match a preset referenced hearing curve on the referenced hearing curve graph, so that the hearing curve preset value is correspondingly produced. Finally, the hearing curve preset value can then be stored in the digital signal processor of the assisting listening device by the algorithmic coefficient storing and processing module.

In view of the abovementioned, an audio signal processing system of the present invention for use in assisting listening devices, can be set via the hearing curve adjusting unit based on the tested hearing curve of a patient, and the preset value can then be stored in the digital signal processor; so that when the patient has to use the assisting listening device in the future, parameters of an audio signal received by the assisting listening device can be adjusted by the hearing curve adjusting unit based on the hearing curve preset value, in order to have the audio signal output to suit the patient's hearing condition.

DETAILED DESCRIPTION OF THE INVENTION

A preferred embodiment of an audio signal processing system and its hearing curve adjusting unit of the present invention for use in assisting listening devices will become more fully understood by reference to the following detailed description thereof when read in conjunction with the attached drawings.

The assisting listening device mentioned in the present invention can be embodied as an earphone for instance; the earphone includes at least a microphone, a speaker and a signal processing circuit. The signal processing circuit usually includes a power circuit and a digital signal processor; audio signals received by the microphone are processed by the digital signal processor before being playback by the speaker; or, audio signals transmitted from other electronic devices are received and processed before being playback by the speaker. The audio signal processing system is disposed in the digital signal processor.

Figure 1:
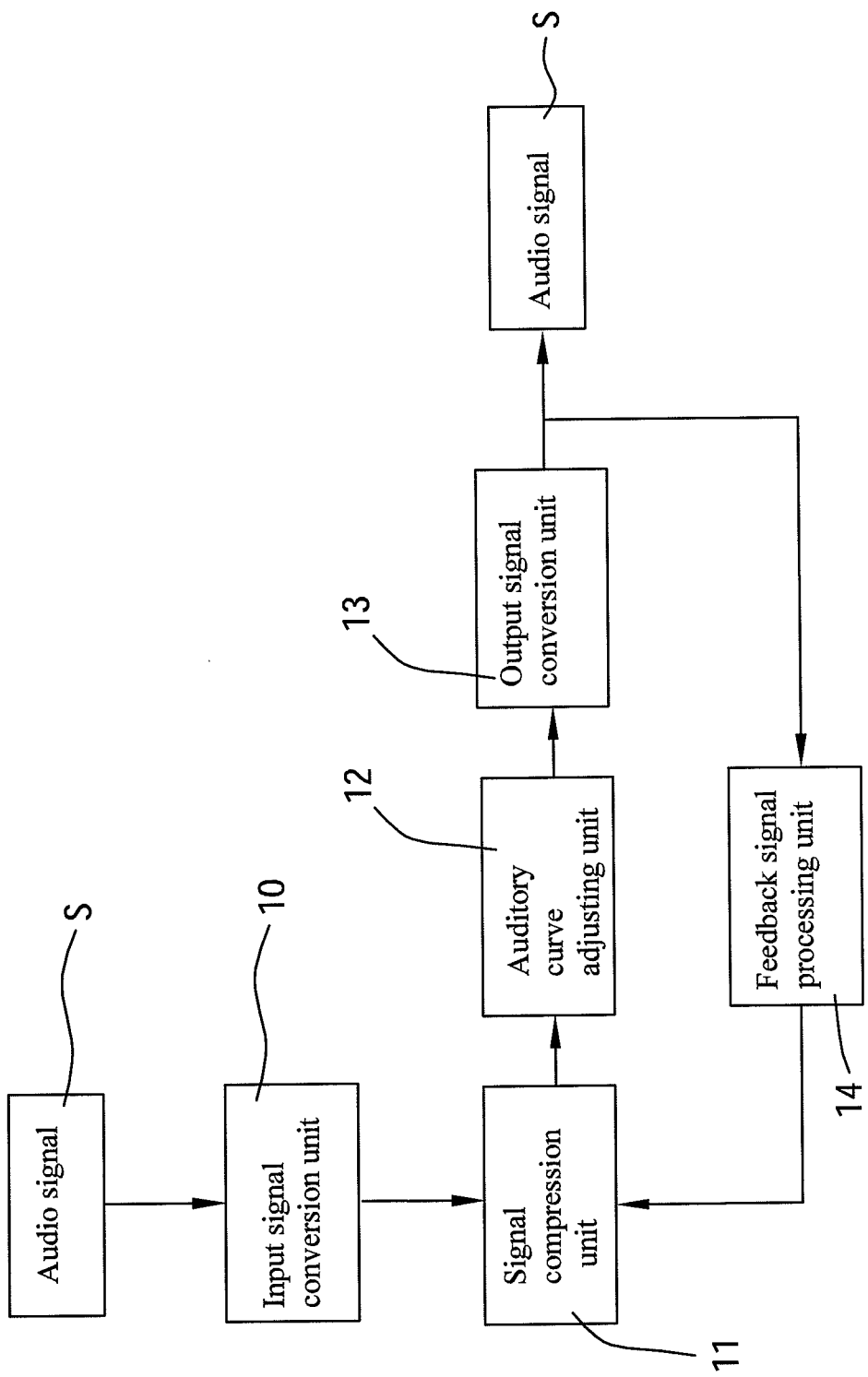
FIG. 1 is a block chart of combination of an audio signal processing system of the present invention.

FIG. 1 is a block chart of combination of an audio signal processing system of the present invention. The audio signal processing system shown in FIG. 1 comprises an input signal conversion unit 10, a signal compression unit 11, a hearing curve adjusting unit 12 and an output signal conversion unit 13. An audio signal S is received and converted from an analog format into a digital format by the input signal conversion unit 10, it is then output to the signal compression unit 11 to be compressed, then it is output to the hearing curve adjusting unit 12 for adjusting parameters of the audio signal S based on an hearing curve preset value in the hearing curve adjusting unit 12, finally it is output to the output signal conversion unit 13 for the audio signal S to be amplified and converted from the digital format into the analog format for output.

The audio signal mentioned above can be for examples, a musical signal output from a music player or a voice signal output from a mobile phone. Parameters of the musical signal or the voice signal are adjusted by the audio signal processing system based on the hearing curve preset value, then an audio signal suitable for the hearing condition of the assisting listening device user is output, and to be playback in the user's ears via the speaker.

The input signal conversion unit 10 not only can convert the audio signal S from the analog format into the digital format, but a sampling percentage and a resolution can be set for the audio signal S. Furthermore, in order to reduce interference by noise or echo when the user is listening to music or voice, the audio signal processing system can further comprises a feedback signal processing unit 14, which can receive the audio signal S output by the output signal conversion unit 13, and have it processed before it is feedback to the signal compression unit 11.

Figure 2:
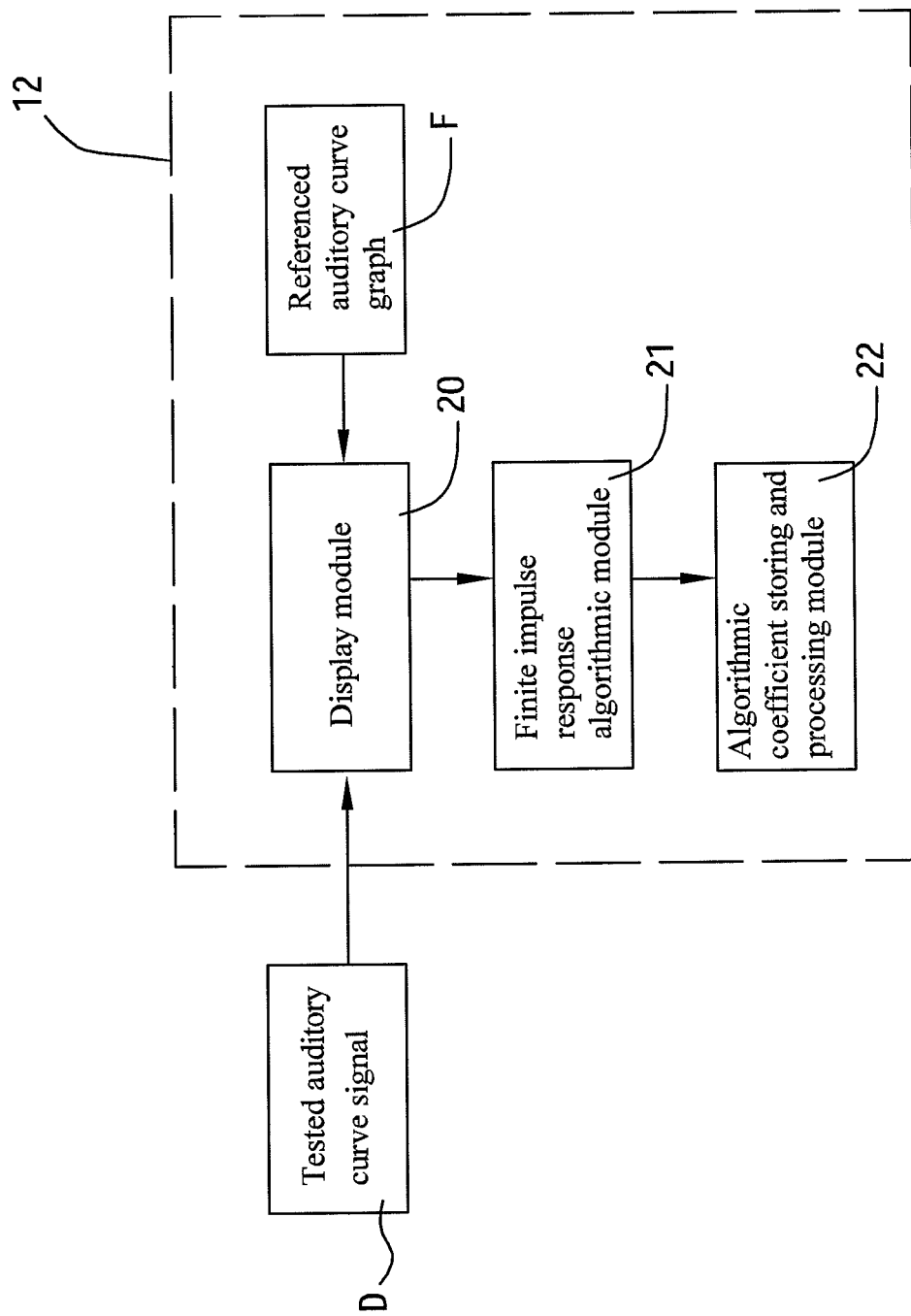
FIG. 2 is a block chart of combination of the hearing curve adjusting unit of the present invention.
Figure 3:
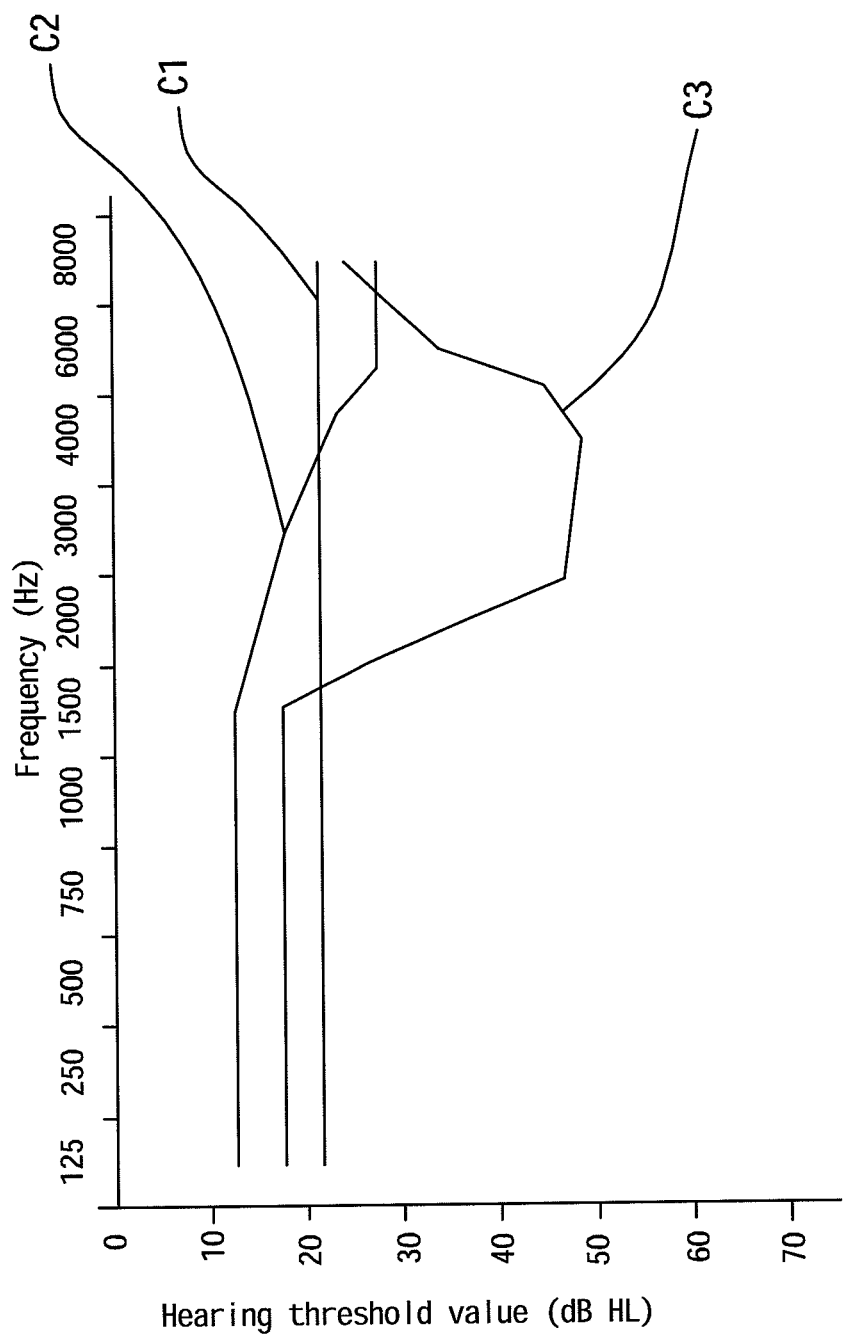
FIG. 3 is a referenced hearing curve graph retrieved by a hearing curve adjusting unit of the present invention.

In order to understand the way the hearing curve preset value is produced by the hearing curve adjusting unit 12 shown in FIG. 1, a combination block chart for the hearing curve adjusting unit shown in FIG. 2, and a referenced hearing curve graph shown in FIG. 3 are provided for explanations. The hearing curve adjusting unit 12 shown in FIG. 2 comprises a hearing curve integration and display module 20, a finite impulse response algorithmic module 21 and an algorithmic coefficient storing and processing module 22. During a setting stage of the hearing curve adjusting unit 12, the hearing curve integration and display module 20 receives a tested hearing curve signal D and a referenced hearing curve graph F, and converts the tested hearing curve signal D to be shown on the referenced hearing curve graph F, and then displayed by a graphic interface. The tested hearing curve signal D can be calculated by finite impulse response filter algorithms via the finite impulse response algorithmic module 21 to produce a filter coefficient matrix; and by adjusting the coefficients of the filter coefficient matrix, the tested hearing curve can be adjusted in order to match a preset referenced hearing curve (C1 to C3) on the referenced hearing curve graph F, so that the hearing curve preset value is correspondingly produced. Finally, the hearing curve preset value can then be stored in the digital signal processor by the algorithmic coefficient storing and processing module 22; parameters of an audio signal transmitted to the audio signal processing system can be adjusted based on the hearing curve preset value.

Figure 4:
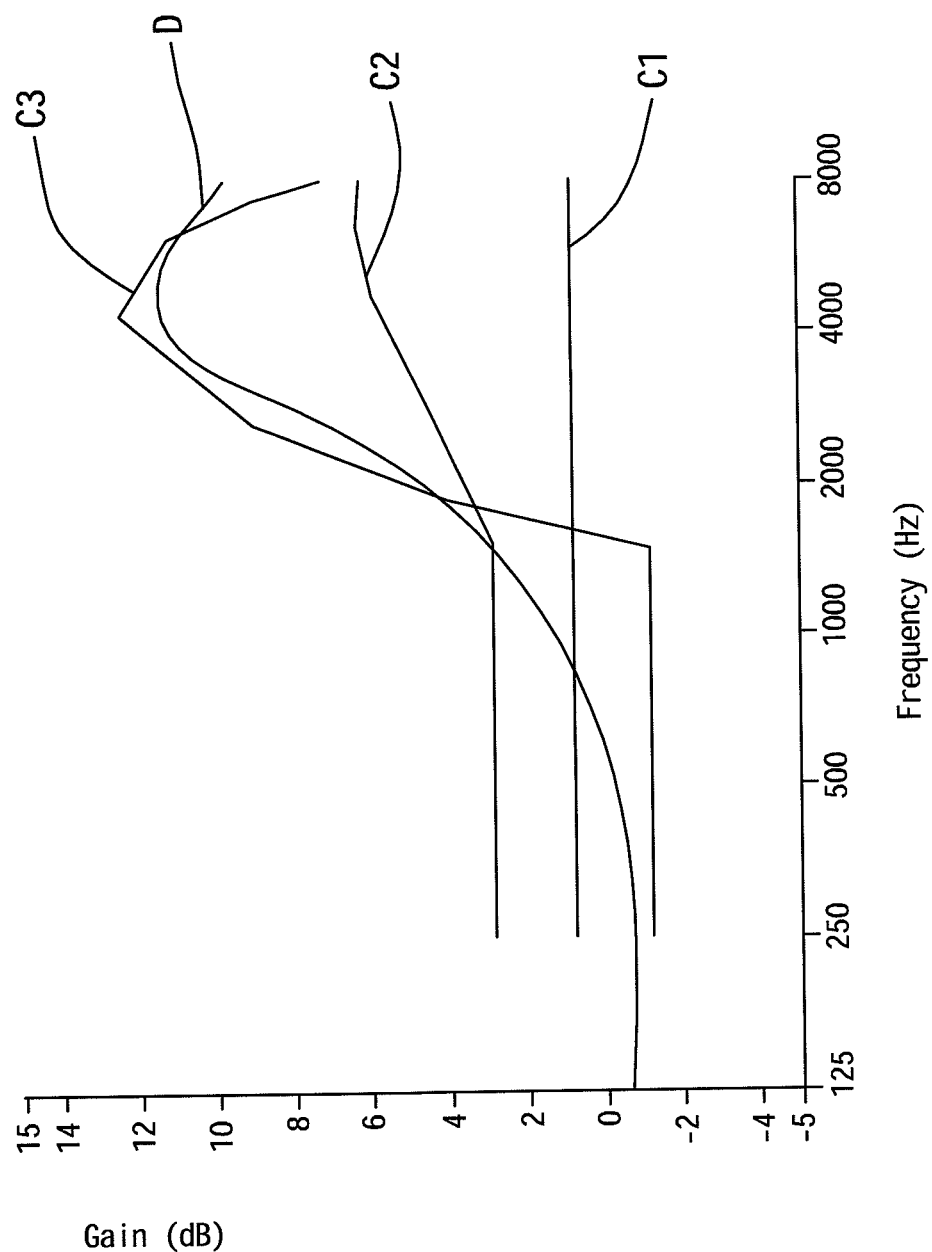
FIG. 4 is graph of referenced hearing curves of FIG. 3 after being calculated and converted.

Referring to FIG. 3, the referenced hearing curve graph F includes three preset referenced hearing curves (C1 to C3) which respectively represent hearing curves for normal hearing ability, mild hearing loss and moderate hearing loss; they are then calculated by weighting algorithms using an hearing adjusting program, so that the three preset referenced hearing curves in FIG. 3 are converted to three hearing curves as shown in FIG. 4 which respectively represent normal hearing ability, mild hearing loss and moderate hearing loss. Besides the three preset referenced hearing curves, the tested hearing curve signal D can also be shown on the graph and displayed via a graphic interface.

When the tested hearing curve signal D mentioned above is converted to be shown via a graphic interface, it can be converted by finite impulse response algorithms into forty two frequency bands, the forty two frequency bands can then be arranged as a filter coefficient matrix. If the hearing signal processing system 12 is used for adjustment for a patient with moderate hearing loss, personnel responsible for an hearing adjusting program can adjust the parameters of the tested hearing curve signal D closed to the parameters of the preset referenced hearing curve C3, by adjusting the forty two frequency bands of the filter coefficient matrix, and have the hearing curve value of the tested hearing curve signal D stored in the algorithmic coefficient storing and processing module 22. Therefore, when an audio signal is input into an hearing curve adjusting unit 12 as shown in FIG. 2, the parameters of the audio signal S can then be adjusted by the hearing curve adjusting unit 12 based on the hearing curve preset value; so that the audio signal S can be suitably adjusted according to the sense of hearing of a patient with mild hearing loss, then the audio signal is output to the patient's meatus auditorius via the speaker of the assisting listening device.

In conclusion, an audio signal processing system of the present invention can be set via the hearing curve adjusting unit based on the tested hearing curve of a patient; so that parameters of an hearing signal transmitted to the audio signal processing system later can be adjusted by the hearing curve adjusting unit based on the hearing curve preset value; therefore an audio signal most suitable for the patient's hearing condition can be output. In comparing to existing technology, the present invention provides simpler setting method, so that patients with mild or moderate hearing loss can have audio signals output most suitable for their hearing conditions, and therefore can have more enjoyment of hearing.

Note that the specifications relating to the above embodiments should be construed as exemplary rather than as limitative of the present invention, with many variations and modifications being readily attainable by a person of average skill in the art without departing from the spirit or scope thereof as defined by the appended claims and their legal equivalents.

What is claimed is:

1. An audio signal processing system for an assisting listening device comprising:

an input signal conversion unit receiving an audio signal and converting the audio signal from an analog format into a digital format;

a signal compression unit receiving the audio signal output by the input signal conversion unit, and having the audio signal compressed;

a hearing curve adjusting unit receiving the audio signal output by the signal compression unit, and adjusting parameters of the audio signal based on a hearing curve preset value in the hearing curve adjusting unit; and an output signal conversion unit receiving the audio signal output by the hearing curve adjusting unit, and the audio signal is amplified and converted from the digital format into the analog format for output.

2. The audio signal processing system as claimed in claim 1, wherein the input signal conversion unit sets a sampling percentage and a resolution for the audio signal.

3. The audio signal processing system as claimed in claim 1, further comprises a feedback signal processing unit for receiving the audio signal output by the hearing curve adjusting unit, its noise and echo are reduced before the audio signal is feedback to the signal compression unit.

4. A hearing curve adjusting unit disposed in an audio signal processing system for use in an assisting listening device, comprising:

a hearing curve integration and display module receiving a tested hearing curve signal and a referenced hearing curve graph, and converting the tested hearing curve signal to be shown on the referenced hearing curve graph, and displayed by a graphic interface;

a finite impulse response algorithmic module, with which the tested hearing curve signal is calculated by finite impulse response filter algorithms to produce a filter coefficient matrix; and by adjusting coefficients of the filter coefficient matrix, the tested hearing curve can be adjusted in order to match a preset referenced hearing curve on the referenced hearing curve graph, so that a hearing curve preset value is correspondingly produced; and an algorithmic coefficient storing and processing module storing the hearing curve preset value in a digital signal processor of the assisting listening device.

5. The hearing curve adjusting unit as claimed in claim 4, wherein three preset referenced hearing curves are shown on the referenced hearing curve graph respectively represent hearing curves of normal hearing ability, mild hearing loss and moderate hearing loss.

6. The hearing curve adjusting unit as claimed in claim 4, wherein the tested hearing curve signal is converted by the finite impulse response algorithmic module into forty two frequency bands, then the forty two frequency bands are arranged as the filter coefficient matrix, and forty two values in the filter coefficient matrix are adjusted by an operator to match the corresponding preset referenced hearing curve.

* * * * *